(12) United States Patent
Abrahmsohn

(10) Patent No.: US 8,828,452 B2
(45) Date of Patent: Sep. 9, 2014

(54) METHOD FOR PAIN CONTROL

(76) Inventor: Glenn Abrahmsohn, Key Biscayne, FL (US)

( * ) Notice: Subject to any disclaimer, the term of this patent is extended or adjusted under 35 U.S.C. 154(b) by 628 days.

(21) Appl. No.: 12/275,056

(22) Filed: Nov. 20, 2008

(65) Prior Publication Data
US 2010/0124575 A1 May 20, 2010

Related U.S. Application Data

(63) Continuation-in-part of application No. 12/124,781, filed on May 21, 2008.

(60) Provisional application No. 60/939,540, filed on May 22, 2007.

(51) Int. Cl.
| A01N 59/00 | (2006.01) |
| A61K 33/00 | (2006.01) |
| A61K 45/06 | (2006.01) |
| A61K 31/167 | (2006.01) |

(52) U.S. Cl.
CPC ............... *A61K 33/00* (2013.01); *A61K 45/06* (2013.01); *A61K 31/167* (2013.01)
USPC .......................................... 424/717; 424/715

(58) Field of Classification Search
CPC .............................. A61K 31/167; A61K 33/00
USPC ................................................... 424/717, 715
See application file for complete search history.

(56) References Cited

U.S. PATENT DOCUMENTS

| 5,192,527 | A | * | 3/1993 | Abrahmsohn | ................ | 424/678 |
| 5,209,724 | A | * | 5/1993 | Dhaliwal et al. | ............... | 424/686 |
| 5,693,312 | A | | 12/1997 | Stroppolo et al. | | |
| 2005/0234013 | A1 | * | 10/2005 | Parsons | ........................... | 514/54 |

FOREIGN PATENT DOCUMENTS

WO          93/00932 A1    1/1993

OTHER PUBLICATIONS

Nielsen et al. (Eur. J. Pharm. Sci. 2005, 24, 433-440).*
Acosta, Alvaro E., et al., Clinical Parameters of Tumescent Anesthesia in Skin Cancer Reconstructive Surgery, Arch Dermatol., 133:451-454 (1997).
Armel, Harvey E., et al., Alkalinization of Local Anesthesia With Sodium Bicarbonate—Preferred Method of Local Anesthesia, Urology, 43(1):101 (1994).
Arndt, Kenneth A., et al., Minimizing the Pain of Local Anesthesia, Plastic and Reconstructive Surgery, 72(5):676-679 (1983).
Bonhomme, Laurence, et al., Stability of Epinephrine in Alkalinized Solutions, Annals of Emergency Medicine, 19(11):1242/31-1244/33 (1990).
Christoph, Richard A., et al., Pain Reduction in Local Anesthetic Administration Through pH Buffering, Annals of Emergency Medicine, 17(2):117/27-121/31 (1988).
Fiscella, R.G., et al., Cocaine Hydrochloride Topical Solution Prepared for Ophthalmic Use, American Journal of Hospital Pharmacy, 50:1572-1574 (1993).
Houle, G.L., et al., A Comparison Between Lignocaine-Carbon Dioxide Base for Epidural Anaesthesia During Vaginal Delivery, British Journal of Anaesthia, 43(2):1145-1148 (1971).
Johnson, Mark D., et al., Reversal of Bupivacaine Epidural Enesthesia by Intermittent Epidural Injections of Crystalloid Solutions, Anesth. Analg. 70:395-399 (1990).
Jones, S.E.F., et al., Anaesthesia for Insertion of Bone-Anchored Hearing Aids in Children: A 7-Year Audit, Anaesthesia, 56:777-798 (2001).
Klein, Jeffrey A., Anesthetic Formulation of Tumescent Solutions, Dermatologics Clinics, 17(4):751-759 (1999).
Lam, D.T., et al., Extension of Epidural Blockade in Labour for Emergency Caesarean Section Using 2% Lidocaine with Epinephrine and Fentanyl, With or Without Alkalinisation, Anaesthesia, 56:777-798 (2001).
Manka, R.L., et al., Sodium Bicarbonate Reduces Pain Associated with Ophthalmic Nerve Blocks, Retractive & Corneal Surgery, 7:186-187 (1991).
McKay, Warren, et al., Sodium Bicarbonate Attenuates Pain on Skin Infiltration with Lidocaine, with or without Epinephrine, Anesth. Analg. 66:572-4 (1987).
Metzinger, Stephen E., et al., Local Anesthesia in Rhinoplasty: A New Twist?, ENT Journal, 71(8):405-406 (1992).
Metzinger, Stephen E. et al., Local Anesthesia in Blepharoplasty: A New Look?, South Med. J., 87(2):225-7 (1994).
Milner, Q.J.W., et al., Alkalinization of Amide Local Anaesthetics by Addition of 1% Sodium Bicarbonate Solution, European Journal of Anaesthesiology, 17:38-42 (2000).
Peterfreund, Robert A., pH Adjustment of Local Anesthetic Solutions with Sodium Bicarbonate: Laboratory Evaluation of Alkalinization and Precipitation, Reg. Anesth., 14(6):265-10 (1989).
Ririe, D.G., et al., Effect of Alkalinization of Lidocaine on Median Nerve Block, British Journal of Anaesthesia, 84(2):163-8 (2000).
Sakura, S., et al., Quantitative and Selective Assessment of Sensory Block During Lumbar Epidural Anaesthesia with 1% or 2% Lidocaine, British Journal of Anaesthesia, 81(5):718-722 (1998).
Sakura, S., et al., Recurrent Neurological Symptoms in a Patient Following Repeat Combined Spinal and Epidural Anaesthesia, 88(1):141-143 (2002).
Sinnott, Catherine J., et al., Addition of Sodium Bicarbonate to Lidocaine Decreases the Duration of Peripheral Nerve Block in the Rat, Anesthesiology, 93(4):1045-1052 (2000).
Steinbrook, Richard A., et al., Effects of Alkalinization of Lidocaine on the Pain of Skin Infiltration and Intravenous Catheterization, J. Clin. Anesth., 5:456-458 (1993).

(Continued)

Primary Examiner — Gina C Justice
Assistant Examiner — Genevieve S Alley
(74) Attorney, Agent, or Firm — Ted Whitlock; Richard Dulik

(57) ABSTRACT

Methods for providing post-operative pain control or relief to a patient are disclosed. Methods include, for example, administering bicarbonate to an area of a patient during a surgical or dental procedure, near completion of a surgical or dental procedure or immediately following a surgical or dental procedure, in an area previously administered or containing a regional or local anesthetic in an amount sufficient to provide the patient with pain control or relief for a period of time after the surgical or dental procedure.

32 Claims, 1 Drawing Sheet

(56) References Cited

OTHER PUBLICATIONS

Stewart, James H., et al., Neutralized Lidocaine with Epinephrine for Local Anesthesia, J. Dermatol. Surg. Oncol. 15:1081-1083 (1989).

Zahl, Kenneth, et al., pH-Adjusted Bupivaccaine and Hyaluronidase for Peribulbar Block, Anesthesiology, 72:230-232 (1990).

Carvalho, et al., Local Infiltration of Epinephrine-Containing Lidocaine with Biocarbonate Reduces Superficial Bleeding and Pain During Labor Epidural Catheter Insertion: A Randomized Trial, International Journal of Obstetric Anesthesia, 2007, 16:116-121.

Wong, et al., On the Mechanisms of Potentiation of Local Anesthetics by Biocarbonate Buffer: Drug Structure-Activity Studies on Isolated Peripheral Nerve, Anes. Analg., 1993, 76:131-143.

Bräu, M.E., et al., Local Anesthetics Potently Block a Potential Insensitive Potassium Channel in Myelinated Nerve, J. Gn. Physiol., 1995, 105:485-505.

Christoph, R.A., et al., Pain Reduction in Local Anesthetic Administration Through pH Buffering, Annals of Emergency Medicine, 1988, 17:117/27-30/120.

Conouris, G.A., et al., Potentiation of the Nerve-Depressant Effect of Local Anaesthetics by Carbon Dioxide, Nature, 1964, 204:57-59.

Difazio, C.A., et al., Comparison of pH-Adjusted Lidocaine Solutions for Epidural Anesthesia, Anesth. Analg., 1986, 65:760-4.

Galindo, A., pH-Adjusted Local Anesthestics: Clinical Experience, Regional Anestheria, 1983, 8:35-36.

Martin, R., et al., Effects of Carbon Dioxide and Epineprine of Serum Levels of Lidocaine After Epidural Anaesthesia, Canad. Anaesth. Soc. J., 1981, 28:224-227.

McKay, W., et al., Sodium Bicarbonate Attenuates Pain on Skin Infiltration with Lidocaine, with or without Epinephrine, Anesth. Analg., 1987, 66:572-4.

Ritchie, J.M., et al., On the Mode of Action of Local Anesthetics, 1966, Annu. Rev. Pharmacol., 6:405-430.

Ritchie, J.M., et al., The Active Structure of Local Anesthetics, The Journal of Pharmacology and Experimental Therapeutics, 1965, 150:152-159.

Shnider, S.M., et al., The Kinetics of Transfer of Lidocaine (Xylocaine) Across the Human Placenta, Anesthesiology, 1968, 29:944-950.

Strobel, G.E., et al., The Effects of pH Gradients on the Action of Procaine and Lidocaine in Intact and Desheathed Sciatic Nerves, The Journal of Pharmacology and Experimental Therapeutics, 1970, 172:1-17.

Buckley, F.P., et al., Acid and Alkaline Solutions of Local Anesthetics: Duration of Nerve Block and Tissue pH, Anesth. Analg., 1985, 64:477-82.

Buckley, F.P., et al., pH of Solution and Duration of Local Anesthetic Block, Regional Anesthesia, 1983, 8:36.

\* cited by examiner

METHOD FOR PAIN CONTROL

RELATED APPLICATIONS

This application is a continuation-in-part of U.S. application Ser. No. 12/124,781, filed May 21, 2008, which claims the benefit of priority to U.S. provisional application No. 60/939,540, filed May 22, 2007, all of which applications are expressly incorporated herein by reference.

INTRODUCTION

Anesthetic agents are pharmacologically active agents that block nerve conduction when applied in therapeutically effective amounts. Anesthetics can be used for local, regional or systemic application. Anesthetics may be applied by injection, ointments, jellies, pastes, topical solutions and suspensions or other forms.

SUMMARY OF THE INVENTION

The invention is based in part on a regional or local anesthesia that can be converted to extend or provide pain (chronic or acute) control or relief. Administration of an inorganic or organic salt agent, such as a bicarbonate (e.g., sodium bicarbonate, 4.8%, pH 7.8-8.2), a buffered phosphated nitrated salt, to a patient that has previously been administered a regional or local anesthesia alters the regional or local anesthesia so as to provide or extend pain (chronic or acute) control in the patient.

The invention therefore provides methods for providing or extending pain (chronic or acute) control or relief to a patient. In one embodiment, a method includes administering an inorganic or organic salt agent (e.g., bicarbonate) to an area of a patient, wherein the area has previously been administered or contains a regional or local anesthetic, and wherein the amount of inorganic or organic salt agent (e.g., bicarbonate) administered is sufficient to provide the patient with pain (chronic or acute) control or relief for a period of time. In another embodiment, a method includes administering a regional or local anesthetic to the patient; and administering an inorganic or organic salt agent (e.g., bicarbonate) to an area of the patient that contains the regional or local anesthetic, and wherein the amount of inorganic or organic salt agent (e.g., bicarbonate) administered is sufficient to provide the patient with pain (chronic or acute) control or relief for a period of time. In an additional embodiment, a method includes administering a regional or local anesthetic to the patient during a surgical or dental procedure, near completion of a surgical or dental procedure or immediately following a surgical or dental procedure; and administering an inorganic or organic salt agent (e.g., bicarbonate) into the area of the patient administered the regional or local anesthetic, wherein the amount of inorganic or organic salt agent (e.g., bicarbonate) administered is sufficient to provide the patient with pain (chronic or acute) control or relief for a period of time after the surgical or dental procedure. In a further embodiment, a method includes administering a regional or local anesthetic to a patient during a surgical or dental procedure, near completion of a surgical or dental procedure or following a surgical or dental procedure; and administering an inorganic or organic salt agent (e.g., bicarbonate) into the area of the patient administered the regional or local anesthetic, wherein the amount of inorganic or organic salt agent (e.g., bicarbonate) administered is sufficient to extend pain (chronic or acute) control or relief to the patient for a period of time.

The methods of the invention include methods that provide or extend pre- or post-operative pain (chronic or acute) control. Thus, for example, in various aspects of the invention, an inorganic or organic salt agent (e.g., bicarbonate) such as a bicarbonate (e.g., sodium bicarbonate, 4.8%, pH 7.8-8.2) or buffered phosphated nitrated salt, is administered to a patient in need of pain control or extension of pain control that has been administered a regional or local anesthetic. The methods of the invention may also be practiced during a surgical or dental procedure, near completion of a surgical or dental procedure or immediately following a surgical or dental procedure. Thus, for example, in various aspects of the invention, a patient is provided with or extended pain (chronic or acute) control during a surgical or dental procedure or following a surgical or dental procedure by appropriate administration of an inorganic or organic salt agent (e.g., bicarbonate).

DETAILED DESCRIPTION OF THE INVENTION

Figure 1:
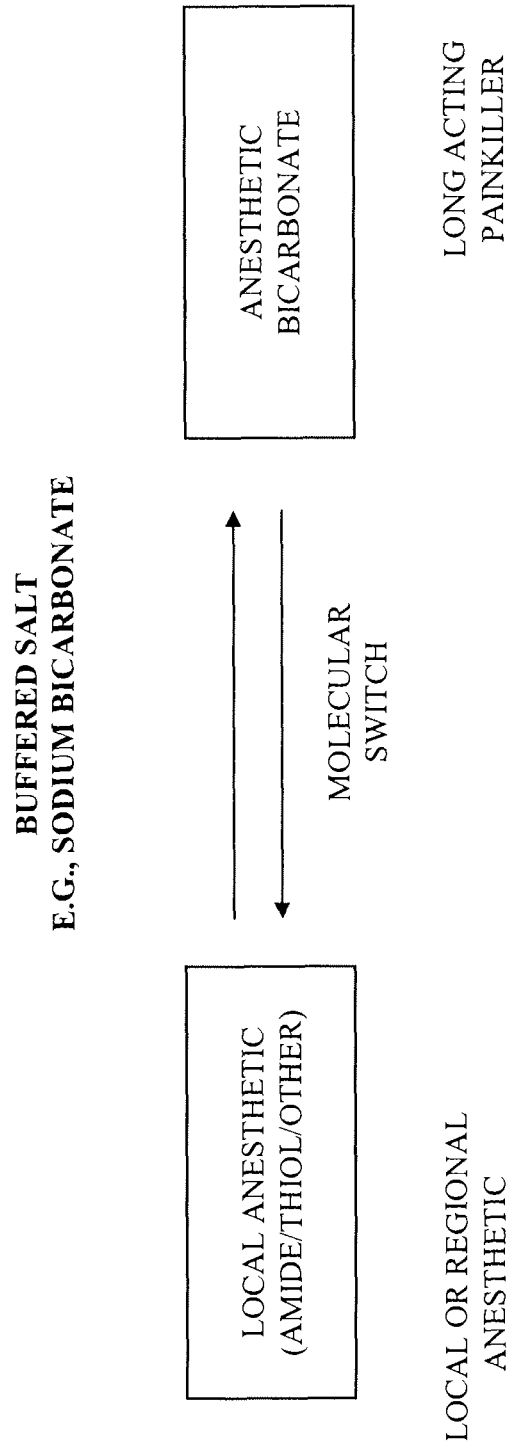
FIG. 1 shows a schematic diagram of a proposed mechanism.

The invention methods provide or extend pain control or relief of regional and local anesthetics. The term "anesthetic" or "anesthesia" used herein refers to a substance that inhibits, reduces, prevents or blocks pain sensation.

A "regional" or "local" anesthetic means an anesthetic having an effect limited to a given area or a part of the body of a patient that remains conscious, as opposed to a general anesthesia where a subject loses consciousness—although a patient may be sedated to relax the patient. A regional anesthetic affects a large part of the body. A local anesthetic affects a smaller or specific part of the body.

Regional anesthesia generally involves the administration of anesthetics to block the nerve supply to a specific part of the body, such as a limb (e.g., leg, arm, lower part of the body, etc.), so a patient does not feel pain in that specific part of the body, but retains sensation in other parts of the body. Specific non-limiting examples of regional anesthetics include epidural anesthesia, spinal anesthesia, brachial plexus blocks, and intravenous regional techniques (e.g., Bier blocks). Regional anesthesia further include nerve blocks that affect major peripheral nerves such as femoral and sciatic nerves.

Local anesthesia generally involves administration of anesthesia to block peripheral nerves at the region or area in which is it desired to suppress pain. A local anesthetic is typically administered by injection or applied to a body surface (e.g., topically via a liquid, paste, ointment, jelly or cream), and then diffuses into nerves where it inhibits the propagation of one or more of pain, muscle contraction, regulation of blood circulation and other body functions. Relatively high doses or concentrations of anesthesia inhibit all sensation (pain, touch, temperature, etc.) as well as muscle control. Lower doses or concentrations of anesthetic can inhibit pain sensation while minimizing the effect on muscle control.

Anesthesia administered regionally or locally therefore includes, among others, surface anesthesia, infiltration, field block anesthesia, nerve block anesthesia, intravenous regional anesthesia, spinal anesthesia and epidural anesthesia. Surface anesthesia involves topical administration to the skin or mucous membranes such as those found in the nose, mouth, throat, tracheo-bronchial tree, esophagus and the genitourinary tract. Infiltration anesthesia typically is an injection of anesthetic directly into the desired tissue. This anesthesia can be superficial so as to include only the skin or include deeper structures including intra-abdominal organs. Infiltration or other anesthetic techniques permit effective anesthesia delivery without disruption of normal body functions. Field block regional anesthesia typically is a subcutaneous injection of local anesthetic to interrupt nerve transmission proximal to the site to be anesthetized. Nerve block regional anesthesia typically involves injection of anesthetic into or about individual or peripheral nerves or nerve plexus thereby affecting larger areas. Intravenous regional anesthesia typically involves injection into a vein of an extremity previously exsanguinated and kept exsanguinated. Spinal anesthesia typically involves injection of anesthetic into the lumbar subarachnoid space. Epidural anesthesia typically involves injection of anesthetic into the epidural space.

Regional and local anesthetics useful in practicing the methods of the invention include a large number of compounds. Specific non-limiting examples of regional and local anesthetics include editocaine, hexylcaine, iontocaine, decicaine, dibucaine, dyclonine, pramoxine, proparacaine and oxybuprocaine (Benoxinate). Anesthetics include amino amides and opiates/opioids. Specific non-limiting examples of amino amide anesthetics include bupivicaine (Marcaine), levobupivicaine, lidocaine, lidocaine derivatives (e.g., N-(2, 6-Dimethylphenylcarbamoylmethyl)triethylammonium bromide, also referred to as QX-314, a quaternary derivative of lidocaine, 2-(trimethylamino)-N-(2,6-dimethylphenyl)acetamide also referred to as QX-222, and N-beta-phenylethyl lidocaine quaternary ammonium bromide), mepivacaine, prilocaine, ropivicaine, articaine (Septocaine) and trimecaine. Prilocaine and articaine (Septocaine) have thiol rings. Specific non-limiting examples of opiates/opioids include fentanyl and morphine. Anesthetics include esters or amides of benzylic acid derivatives, such as benzocaine, chloroprocaine, cocaine, tetracain (Pontocaine) and procaine (Novocaine). Anesthetics include prodrugs.

Anesthetics can be in a hydrochloride acid-addition salt. Typically, regional or local anesthetics are administered in a solution (e.g., aqueous solution), for example, a form of hydrochloride acid-addition salt in an aqueous solution.

Doses can be based upon current existing treatment protocols, empirically determined, determined using animal disease models or in human clinical studies. For example, a regional or local anesthetic is typically administered in a solution from about 0.5 to 5% and in other mixtures of up to 20% or 30% or more by weight/volume. The amount administered depends on the route or area for administration. For application to an oral cavity (e.g., mouth or buccal tissue), the amount administered generally is no more than 6 ml of a 2% solution.

Typical amounts of lidocaine that are commercially available as the hydrochloride and is used in preparations in about 0.5 to about 20% by weight, volume (up to about 7 mg/kg body weight), some with and some without epinephrine for infiltration, about 1 to 2% for block and about 5% for topical mucosal anesthesia. Bupivicaine is used commercially as a hydrochloride in solutions from about 0.25 to about 0.75%; chloroprocaine, typically as the hydrochloride in solutions of about 1 to 3%. Ediocaine is typically used as a hydrochloride in solutions of about 1 to 2%. Mepivicaine is typically used in solutions of from about 1 to 3%, optionally with or without levonordenphedrine as a vasoconstrictor. Prilocaine is typically used as the hydrochloride in solution at about 4%, optionally with or without epinephrine as a vasoconstrictor. Procaine is typically used as the hydrochloride in solutions of about 0.25 to 0.5% for infiltration, 0.5% to 2% for peripheral nerve block and 10% for spinal anesthesia. Tetracaine is typically used in solutions as the hydrochloride of about 5% as an ointment and about 2% for application to the mucous membranes or throat. Tetracaine for injection is available in solutions or ampules containing the dry salt, as well as ointments of 5% and creams of 1%.

After a regional or local anesthesia has been administered to the patient, inorganic or organic salt agent is administered. Although not wishing to be bound by any theory, it is believed that a regional or local anesthesia is converted by an inorganic or organic salt agent to an anesthetic which provides or extends pain control or relief (FIG. 1). For example, a bicarbonate can attach to an amide or thiol ring thereby extending anesthetic action or activity. Thus, the inorganic or organic salt agent alters or transforms the regional or local anesthesia into a slow or prolonged release form that functions as a prolonged regional or local anesthetic, thereby providing or extending pain control or relief. Typically, inorganic or organic salt agent that is administered to a patient does not also contain an anesthetic, i.e., is not a mixture of inorganic or organic salt agent and a regional or local anesthetic.

The area or site of inorganic or organic salt agent administration will therefore have some amount of regional or local anesthesia. Thus, the site of administration is typically in relative close proximity to, or within, the area that has previously been administered a regional or local anesthesia or that otherwise contains some amount (e.g., by diffusion, by transport through patient circulation, etc.) of regional or local anesthesia. Specific non-limiting examples of areas of a patient that are appropriate for administration of a regional or local anesthesia and inorganic or organic salt agent include a wound or cut, a surgical (e.g., incision site or area) or dental area (e.g., extracted tooth site or area) or region, torso, stomach, chest, head, scalp, neck, face, nose, ear, shoulder, back, arm, leg, thigh, ankle, knee, foot, toe, hand, wrist, finger, buttocks, groin, and joints. Accordingly, administration of regional or local anesthesia, or an inorganic or organic salt agent, can be to or near a wound or cut, a surgical or dental region such as to an incision or site of a surgical or dental procedure (e.g., extracted tooth site), or any other affected area, tissue, organ of the body (e.g., torso, stomach, chest, head, scalp, neck, face, nose, ear, shoulder, back, arm, leg, thigh, ankle, knee, foot, toe, hand, wrist, finger, buttocks, groin, and joints).

The term "inorganic or organic salt agent" refers to a salt. Such salts include those capable of being adjusted to a pH of about 7 or greater. A salt is typically an alkali or alkaline earth metal salt of an inorganic or organic acid, such as a salt of a weak acid, and strong base, or weak base. In order to achieve a pH of about 7 or greater, a salt is typically a salt of a weak acid and strong base, or of a salt of a weak acid and a weak base.

Typical cations of the salt are sodium, potassium, calcium and magnesium. Typical anions are monovalent inorganic anions such as fluoride, bromide and chloride; multivalent organic anions such as carbonate, hydrogen carbonate; and multivalent inorganic anions such as sulphate, and phosphate.

Non-toxic inorganic anions of organic acids include anions of mono-like and dibasic organic acids such as acetate, gluconate and mono- or di-carboxylic acids.

Exemplary specific examples to administer to a subject that has been previously administered or that contains a regional or local anesthetic in order to provide or extend pain control or relief include bicarbonates (e.g., sodium bicarbonate, 4.8%, pH 7.8-8.2, such as with carbon dioxide), and buffered phosphated nitrated salts.

Amounts of inorganic or organic salt agents to administer to a subject. Amounts of inorganic or organic salt agent salt administered are in a 1:1, 2:1, 3:1, 4:1, 5:1, 6:1, 7:1, 8:1, 9:1 10:1 ratio to the regional or local anesthetic administered. Typical amounts of inorganic or organic salt agent salt administered is in a 1:1 ratio to the regional or local anesthetic administered. Typical amounts of inorganic or organic salt agent salt (e.g., bicarbonate) administered are from about 1% to 15%, or about 2 to 10% or about 4 to 10%. Typically, the salt is present, depending upon solubility, in an amount of approximately 1 molar in aqueous solution. In the case of sodium bicarbonate, a 1 molar, or meq/ml (84 mgs/ml) solution has a pH of about 7.8-8.2. Such a solution can be conveniently contained in dosage unit of a size of approximately 1.8 ml for application to oral cavity, for example.

A "sufficient" or "effective" amount as used herein means an amounts that achieves or is likely to achieve a desired effect or outcome. Thus, in a method of the invention a sufficient or effective amount will provide or extend pain control or relief in a given patient to a measurable or detectable extent. In particular embodiments, pain control or relief provided to the patient has a duration of about 0.5-72 hrs, about 0.5-48 hrs, about 0.5-24 hrs, or about 1-12 hrs.

Sufficient or effective amounts depend upon the desired effect, the anesthetic administered to the patient, the inorganic or organic salt agent administered that provides or extends pain control or relief to the patient, the location of administration and the form administered. Of course, as is typical for any treatment or therapy, different patients will exhibit different responses to treatment and some patients may not respond or respond inadequately to a particular treatment. Since every treated patient may not respond to a particular method, the methods set forth herein are not required to achieve pain control or relief in each and every patient, or a given population so treated. Accordingly, an amount sufficient or an amount effective means sufficiency or effectiveness in a particular patient, not a group of subjects or the general population.

Administration of regional or local anesthetic, or inorganic or organic salt agent, in accordance with the invention methods include any mode (e.g., bolus dose or a slow or delayed release) or route of administration or delivery. Exemplary delivery and administration routes include oral (buccal, sublingual, alimentary, mucosal), intravenous, intrarterial, intradermal, parenteral (e.g., subcutaneous, intramuscular), intratumor, intra-pleural, topical (dermal), transdermal, transmucosal, intra-cranial, intra-spinal, intra-tracheal, epidural, intra-ocular, intracavity, iontophoretic, rectal, vaginal, intrauterine, ophthalmic, optical (e.g., corneal), intraglandular, intraorgan, intralymphatic, intrapulmonary, intranasal and intrathecal.

Typically, an inorganic or organic salt agent will be administered in a fluid (e.g., aqueous or non-aqueous solution) having a pH equal to or greater than about pH 7, for example between about pH 7-11 and more typically between about pH 7 to 8.5 (e.g., 7.8-8.2, such as with carbon dioxide). There is no upper limit to the pH. In practice, upper limit of pH is determined by the nature of the salt, any buffer or base present, and the concentration of inorganic or organic salt agent. Additionally, skin sensitivity to basic substances is such that a pH typically not greater than 10 and more typically not greater than 9 is used.

A desired pH can be maintained in a buffer. For example, a buffer can maintain a pH of about 7 or more, or a pH of at least 7.8, or a pH from about 7 to 8.5. Typical buffers include inorganic and organic buffers including phosphate, citrate, bicarbonate and the like. The upper limit of the pH is not limited except that, the upper limit of the pH can be affected by the nature of the salt, and any buffer, and concentration of base that may be used to adjust the pH. A desired pH can be obtained using carbon dioxide, for example.

A regional or local anesthetic, or inorganic or organic salt agent, can be administered in a non-toxic pyrogen free, fluid mixture. The term "non-toxic" used herein means not causing death of a patient or undesirable side effects, such as permanent damage to a nerve or muscle. Systemic toxicity of agents and anesthetics administered in accordance with the invention are optionally low. The term "pyrogen free" when applied to regional or local anesthetic, or inorganic or organic salt agent suitable for administration to a patient means that the anesthetics and agents do not contain substances known to cause a pyrogenic response. Pyrogens can be removed from mixtures by methods known to one skilled in the art.

Administration of regional or local anesthetic or inorganic or organic salt agent in accordance with the invention methods can be performed during a surgical or dental procedure, or within a specified period of time prior to or after a surgical or dental procedure (e.g., within 72, 48, 24, 12, 6, 2 hours, or less, 60 minutes, 30 minutes, etc.). Administration of regional or local anesthetic or inorganic or organic salt agent in accordance with the invention methods can also be performed multiple times (e.g., 1-10, 1-5 or 1-3 times) per minute, hour, day, week or month. For example, in various embodiments of the invention, an inorganic or organic salt agent is administered to a patient immediately following administration of regional or local anesthetic. In various additional embodiments of the methods of the invention, an inorganic or organic salt agent is administered to a patient within about 1-5, 1-10, 2-10, 5-20, 15-30, 30-60 or 60-120 minutes after administration of regional or local anesthetic.

The method can optionally be used in conjunction with a vasoconstrictor to prolong the duration of the action. For example, an anesthetic can be administered concomitantly with a vasoconstrictor. The term "vasoconstrictor" used here means an agent capable of causing constriction of blood vessels including various sympathomimetic drugs such as epinephrine, norepinephrine, levonordenphedrine and dopamine. Typically, epinephrine is administered in a dilution of 1:100,000 mixed with a solution of lidocaine and supplied in 1.8 ml capsules.

The invention methods are appropriate in any surgical or dental procedure or context in which a local or regional anesthetic is used or has already been administered to a patient. Non-limiting examples of surgical and dental procedures include cancer or tumor surgery, trauma surgery, cosmetic surgery, abdominal surgery, head or neck surgery, orthopedic surgery, back or spine surgery, arthroscopic surgery, brain surgery, ear, nose or throat surgery, eye surgery, amputation, liposuction, rhinoplasty, graft or transplant surgery, a biopsy, skin surgery, breast surgery, prosthetic surgery, fetal surgery, gastroenterologic surgery, thoracic surgery, bladder surgery, heart surgery, liver surgery, pancreas surgery, kidney surgery, lung surgery, gallstone surgery, hernia surgery, shoulder, arm, leg, pelvis, hip, knee, elbow or ankle surgery, uterine or vaginal surgery, blood vessel surgery, prostate surgery, colon or rectal surgery, laser surgery, oral surgery, periodontal surgery, dental implant or tooth repair or extraction. Additional non-limiting examples of surgical procedures include child birth (e.g., natural vaginal birth, in which labor is not induced or labor is induced) and child birth related surgery, such as surgery during childbirth, including cesarean section, episiotomy, etc., and surgery following childbirth, such as labioplasty, stomach tightening, breast augmentation or enlargement, varicose vein treatment, etc.

The invention methods can employ pharmaceutical compositions and formulations. As used herein the terms "pharmaceutically acceptable" and "physiologically acceptable" mean a biologically compatible formulation, gaseous, liquid or solid, or mixture thereof, which is suitable for one or more routes of administration, in vivo delivery or contact. A formulation is compatible in that it does not destroy activity of an active ingredient therein, or induce adverse side effects that far outweigh any therapeutic benefit or effect.

Such formulations include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents.

Cosolvents may be added. Non-limiting examples of cosolvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters.

Supplementary active compounds (e.g., preservatives, antioxidants, antimicrobial agents including biocides and biostats such as antibacterial, antiviral and antifungal agents) can also be incorporated. Preservatives and other additives include, for example, antimicrobials, anti-oxidants, chelating agents and inert gases (e.g., nitrogen).

Preservatives include, for example, EDTA, EGTA, benzalkonium chloride or benzoic acid or benzoates, such as sodium benzoate. Antioxidants include, for example, ascorbic acid, vitamin A, vitamin E, tocopherols, and similar vitamins or provitamins. Antimicrobials include, antibacterial, antiviral, antifungal and antiparasitics that kill or destroy (-cidal) or inhibit (-static) contamination by or growth, infectivity, replication, proliferation, reproduction of the microbial organism.

Pharmaceutical compositions can optionally be formulated to be compatible with a particular route of administration. Thus, pharmaceutical compositions include carriers (excipients, diluents, vehicles or filling agents) suitable for administration by various routes and delivery, regionally, locally or systemically, ex vivo or in vivo, as set forth herein or known to the skilled artisan.

Formulations suitable for parenteral administration include aqueous and non-aqueous solutions, suspensions or emulsions of the compound, which may include suspending agents and thickening agents, which preparations are typically sterile and can be isotonic with the blood of the intended recipient. Non-limiting illustrative examples of aqueous carriers include water, saline (sodium chloride solution), dextrose (e.g., Ringer's dextrose), lactated Ringer's, fructose, ethanol, animal, vegetable or synthetic oils. Examples of non-aqueous solvents are propylene glycol, polyethylene glycol, vegetable oils such as olive oil, and injectable organic esters such as ethyl oleate. Intravenous vehicles include fluid and nutrient replenishers, electrolyte replenishers (such as those based on Ringer's dextrose).

For transmucosal or transdermal administration (e.g., topical contact), penetrants can be included in the pharmaceutical composition. Penetrants include, for example, for transmucosal administration, detergents, bile salts, and fusidic acid derivatives. For transdermal administration, the active ingredient can be formulated into aerosols, sprays, ointments, salves, gels, pastes, lotions, oils or creams.

For oral administration, pharmaceutical compositions include capsules, cachets, lozenges, tablets or troches, as powder or granules. Oral administration formulations also include a solution or a suspension (e.g., aqueous liquid or a non-aqueous liquid; or as an oil-in-water liquid emulsion or a water-in-oil emulsion).

For topical administration, for example, to skin, pharmaceutical compositions typically include ointments, creams, lotions, pastes, gels, sprays, aerosols or oils. Carriers which may be used include Vaseline, lanolin, polyethylene glycols, alcohols, transdermal enhancers, and combinations thereof.

Additional pharmaceutical formulations appropriate for administration are known in the art (see, e.g., Gennaro (ed.), *Remington: The Science and Practice of Pharmacy*, 20$^{th}$ ed., Lippincott, Williams & Wilkins (2000); Ansel et al., *Pharmaceutical Dosage Forms and Drug Delivery Systems*, 7$^{th}$ ed., Lippincott Williams & Wilkins Publishers (1999); Kibbe (ed.), *Handbook of Pharmaceutical Excipients American Pharmaceutical Association*, 3$^{rd}$ ed. (2000); and *Remington's Pharmaceutical Principles of Solid Dosage Forms*, Technonic Publishing Co., Inc., Lancaster, Pa., (1993)).

The term "patient" or "subject" are used interchangeably herein and refer to animals, typically mammals, such as humans, non-human primates (gorilla, chimpanzee, orangutan, macaque, gibbon), domestic animals (dog and cat), farm and ranch animals (horse, cow, steer, goat, sheep, goat, pig), laboratory and experimental animals (mouse, rat, rabbit, guinea pig). Human subjects include children, for example, newborns, infants, toddlers and teens, between the ages of 1 and 5, 5 and 10 and 10 and 18 years, adults between the ages of 18 and 60 years, and the elderly, for example, between the ages of 60 and 65, 65 and 70 and 70 and 100 years.

Patients and subjects include mammals (e.g., humans) in need of treatment, that is, for example, they are at risk of or are experiencing undesirable pain. Such patients and subjects therefore include those that are undergoing a surgical or dental procedure that results or is likely to result in ("at risk of") pain due to the surgical or dental procedure. Patients and subjects can therefore be treated in order to inhibit or reduce the likelihood or risk of developing pain. The result of such treatment can be to provide or extend pain control to the patient or subject.

The invention further provides kits, including regional and local anesthetics, and inorganic or organic salt agents, and pharmaceutical formulations thereof, packaged into suitable packaging material, optionally in combination with instructions for using the kit components, e.g., instructions for providing or extending pain control or relief. Invention kits can include therein a individual container or in a mixture and all of the various containers can be within single or multiple packages that comprise the kit.

The term "packaging material" refers to a physical structure housing the components of the kit. The packaging material can maintain the components sterilely, and can be made of material commonly used for such purposes (e.g., paper, corrugated fiber, glass, plastic, foil, ampules, etc.).

The label or packaging insert can include appropriate written instructions. Thus, in various embodiments, a kit includes a label or packaging insert including instructions for practicing a method of the invention.

Instructions may additionally include indications of a satisfactory clinical endpoint or any adverse symptoms or complications that may occur. Instructions may further include storage information, expiration date, or any information required by regulatory agencies such as the Food and Drug Administration for use in a human subject.

The instructions may be on "printed matter," e.g., on paper or cardboard within the kit, on a label affixed to the kit or packaging material, or attached to a vial or tube containing a component of the kit. Instructions may comprise audio or video medium and additionally be included on a computer readable medium, such as a disk (floppy diskette or hard disk), optical CD such as CD- or DVD-ROM/RAM, magnetic tape, electrical storage media such as RAM and ROM and hybrids of these such as magnetic/optical storage media.

Unless otherwise defined, all technical and scientific terms used herein have the same meaning as commonly understood by one of ordinary skill in the art to which this invention relates. Although methods and materials similar or equivalent to those described herein can be used in the practice or testing of the invention, suitable methods and materials are described herein.

All publications, patents, and other references cited herein are incorporated by reference in their entirety. In case of conflict, the present specification, including definitions, will control.

As used herein, singular forms "a", "and," and "the" include plural referents unless the context clearly indicates otherwise. Thus, for example, reference to "an anesthetic" includes a plurality of anesthetics and reference to "an inorganic or organic salt agent" can include multiple inorganic or organic salt agents, and so forth.

As used herein, reference to a numerical value or numerical range includes reference to a fraction of such values, and whole integers and fractions within or encompassing such ranges of the values or integers within or encompassing ranges unless the context clearly indicates otherwise. Thus, for example, reference to a numerical value of 7 includes reference to 7.1, 7.2, and so forth. Reference to a range of 1-15%, includes 2, 3, 4, 5, 6, 7, 8%, etc., as well as 1.1, 1.2, 1.3, 1.4, 1.5%, etc., 2.1, 2.2, 2.3, 2.4, 2.5%, etc., and so forth. In another example, reference to a unit of time, such as within 72 hours, means within 71, 70, 69, 68 . . . 1 hour, or minutes, e.g., 59, 58, 57, 56, 55 . . . 1 minute, and so forth. In yet another example, reference to a ratio of 2:1 includes 2:1.1, 2:1.2, 2:1.3, 2:1.4, 2.1:1, 2.2:1, 2.3:1, 2.4:1, and so forth.

The invention is generally disclosed herein using affirmative language to describe the numerous embodiments. The invention also specifically includes embodiments in which particular subject matter is excluded, in full or in part, such as substances (e.g., particular anesthetics or inorganic or organic salt agents) or materials, method steps and conditions, protocols, procedures, assays or analysis. Thus, even though the invention is generally not expressed herein in terms of what the invention does not include, aspects that are not expressly included in the invention are nevertheless disclosed.

A number of embodiments of the invention have been described. Nevertheless, it will be understood that various modifications may be made without departing from the spirit and scope of the invention. Accordingly, the following examples are intended to illustrate but not limit the scope of invention described in the claims.

EXAMPLES

| SITE OF OPERATION | 1.5% LIDOCAINE or EQUIVALENT | 0.5% MARCAINE/ 0.5% BUPIVICAINE | |
|---|---|---|---|
| | CONCENTRATION OF AMIDE LOCAL ANESTHESIA | | |
| | | | PAIN CONTROL w/Buffered NaHCo3 4.2%-8.4% use 3 times volume of NaHCo3 |
| Upper abdominal | 30 ml | 30 ml | 30-90 ml |
| Lower abdominal | 20 ml | 20 ml | 20-60 ml |
| Hernias & varicose veins | 20 ml | 20 ml | 20-60 ml |
| Perineal/bladder-neck Operations | 15 ml | 15 ml | 15-45 ml |
| {Cervical plexus blocks | 1% Lido 10-20 ml | 10-20 ml | 10-60 ml} |
| {2nd block-cervical plexus {3rd & 4th cervical vertebrae | 1.0-1.5% Lido 5 ml | 5 ml | 5-15 ml} |
| Intercostal block | 0.5-1% Lido 3-4 ml | 3-4 ml | 3-9 ml |
| Para verterbral somatic n.block | 1% Lido 5 ml | 5 ml | 5-15 ml |
| Brachial plexus | 1.2% 5-10 ml @ ea Site total of 30-40 ml | 5-10 ml @ ea. site total of 30-40 ml | 5-15 ml max @ 90-120 ml |
| Interscalene brachial Plexus block | 1-1.5% Lido 20-40 ml | 20-40 ml | 20-120 ml |
| Superclavicular block | 1-1.5% 20-25 ml | 20-25 ml | 20-75 ml |

-continued

| SITE OF OPERATION | 1.5% LIDOCAINE or EQUIVALENT | 0.5% MARCAINE/ 0.5% BUPIVICAINE | |
|---|---|---|---|
| Nerve block @ elbow | | | |
| Median nerve | 2% Lido 2-3 m. | 2-3 ml | 2-9 ml |
| Radial nerve | 2% Lido 10 ml | 10 ml | 10-30 ml |
| Ulnar nerve | 2% Lido 2 ml | 2 ml | 2-6 ml |
| | CONCENTRATION OF AMIDE LOCAL ANSTHETIC | | |
| | | | AMOUNT OF BUFFERED NaHCo3 |
| Nerve block @ wrist | | | |
| Medial nerve | 2% Lido 1-2 ml | 1-2 ml | 1-6 ml |
| Ulnar nerve | 2% Lido 2 ml | 2 ml | 2-6 ml |
| Radial nerve | 2% Lido 2 ml | 2 ml | 2-6 ml |
| Hand & Digital blocks | | avoid excessive distention & no epi | |
| | 1% 5 ml | 5 ml | 5 ml |
| Femoral nerve block | 1% Lido | 5-10 ml | 5-30 ml |
| Lateral Femoral cutaneous | | | |
| Nerve block | 1% Lido 5-10 ml | 5-10 ml | 5-30 ml |
| Sciatic nerve block | 2% Lido 10-20 ml | 10-20 ml | 10-60 ml |
| Intravenous regional Anesthesia | see article | | =to 3xvolume |
| Epidural anesthesia | 1.5% 10 ml | 0.5% 10 ml | 10-30 ml |
| Continuous epidural Anesthesia | 0.2% Bupivicaine @ rate of 2 ml/hr for 48 hours | 2 ml/hr | 2 ml/hr |
| Spinal anesthesia | 0.5% Amethocaine in 10% Glucose over 20 secs. | 2 ml | 2 ml-plus if needed |

What is claimed is:

1. A method for providing post-operative pain control or relief to a patient comprising administering bicarbonate to an area of a patient during a surgical or dental procedure, near completion of a surgical or dental procedure or immediately following a surgical or dental procedure, wherein the area has previously been administered or contains a solution of regional or local anesthetic at a concentration of up to about 10% to provide anesthetic inhibition of sensation, and wherein the bicarbonate at a concentration of 1 to 15% in solution is administered at a ratio of greater than 1:1 (v/v) to 10:1 (v/v) to the amount of the anesthetic previously administered, wherein said bicarbonate reverses anesthetic inhibition of sensation, except pain sensation, and provides or extends pain control or relief to the patient for a period of time after the surgical or dental procedure.

2. A method for providing post-operative pain control or relief to a patient, comprising:
   a) administering a regional or local anesthetic to the patient which inhibits sensation; and
   b) administering bicarbonate solution to an area of the patient during a surgical or dental procedure, near completion of a surgical or dental procedure or immediately following a surgical or dental procedure,
wherein the area contains the regional or local anesthetic, and wherein the bicarbonate solution administered is in a ratio of greater than 1:1 (v/v) to about 10:1 (v/v) of anesthetic which reverses anesthetic inhibition of sensation, except pain sensation, and provides or extends pain control or relief to the patient for a period of time after the surgical or dental procedure.

3. A method for extending post-operative pain control or relief to a patient in need thereof, comprising
   a) administering a regional or local anesthetic to the patient which inhibits sensation during a surgical or dental procedure, near completion of a surgical or dental procedure or following a surgical or dental procedure; and
   b) administering bicarbonate solution into the area of the patient administered the regional or local anesthetic, wherein the bicarbonate administered is at a ratio of greater than 1:1 (v/v) to about 10:1 (v/v) of anesthetic and reverses anesthetic inhibition of sensation, except pain sensation, in the patient and extends pain control or relief to the patient for a period of time after the surgical or dental procedure.

4. The method of any of claims 1, 2 or 3, wherein the bicarbonate administered does not contain an anesthetic.

5. The method of any of claims 1, 2 to 3, wherein the bicarbonate converts the regional or local anesthetic into a slow or prolonged release regional or local anesthetic.

6. The method of any of claims 1, 2 or 3, wherein the area of the patient comprises the torso, stomach, chest, head, scalp, neck, face, nose, ear, shoulder, back, arm, leg, thigh, ankle, knee, foot, toe, hand, wrist, finger, buttocks, groin, or a joint.

7. The method of any of claims 1, 2 or 3, wherein the area of the patient comprises an incision or cut.

8. The method of any of claims 1, 2 or 3, wherein the bicarbonate is administered to the patient immediately following the surgical or dental procedure, thereby providing or extending post-operative pain control or relief to the patient.

9. The method of any of claims 1, 2 or 3, wherein the bicarbonate is administered multiple times.

10. The method of any of claims 1, 2 or 3, wherein the regional or local anesthetic is administered topically, intradermally, intramuscularly, intravenously, subcutaneously, epidurally, by infusion or by injection.

11. The method of any of claims 1, 2 or 3, wherein the bicarbonate is administered topically, intradermally, intramuscularly, intravenously, subcutaneously, epidurally, by infusion or by injection.

12. The method of any of claims 1, 2 or 3, wherein the amount of bicarbonate administered is in a volume:volume-ratio greater than 2:1, 3:1, 4:1, 5:1, 6:1, 7:1, 8:1, or 9:1, or up to 10:1 to the regional or local anesthetic administered.

13. The method of any of claims 1, 2 or 3, wherein the regional or local anesthetic comprises an opiate, an amide or an amine.

14. The method of any of claims 1, 2 or 3, wherein the regional or local anesthetic comprises a prodrug.

15. The method of any of claims 1, 2 or 3, wherein the regional or local anesthetic comprises editocaine, hexylcaine, iontocaine, decicaine, dibucaine, dyclonine, pramoxine, proparacaine, oxybuprocaine (Benoxinate), bupivicaine (Marcaine), levobupivicaine, lidocaine, a lidocaine derivative, mepivacaine, prilocalne, ropivicaine, articaine (Septocaine), trimecaine, fentanyl, morphine, benzocaine, chloroprocaine, cocaine, tetracain (Pontocaine) and procaine (Novocaine).

16. The method of claim 15, wherein the lidocaine derivative comprises QX-314, QX-222, or N-beta-phenylethyl lidocaine quaternary ammonium bromide.

17. The method of any of claims 1, 2 or 3, wherein the bicarbonate comprises sodium bicarbonate.

18. The method of any of claims 1, 2 or 3, wherein the bicarbonate solution has a pH of greater than about 7.0.

19. The method of any of claims 1, 2 or 3, wherein the bicarbonate solution has a pH of about 7.0-11.0.

20. The method of any of claims 1, 2 or 3, wherein the bicarbonate solution has a pH of about 7.8-8.5.

21. The method of any of claims 1, 2 or 3, wherein the bicarbonate comprises a solution of about 1 to 15% sodium bicarbonate.

22. The method of any of claims 1, 2 or 3, wherein the bicarbonate comprises a solution of sodium bicarbonate, 4.8%, pH 7.8-8.5.

23. The method of any of claims 1, 2 or 3, wherein the pain control or relief provided to the patient following administering bicarbonate has a duration of about 0.5-72 hrs.

24. The method of any of claims 1, 2 or 3, wherein the surgical or dental procedure comprises cancer or tumor surgery, trauma surgery, cosmetic surgery, abdominal surgery, head or neck surgery, orthopedic surgery, back or spine surgery, arthroscopic surgery, brain surgery, ear, nose or throat surgery, eye surgery, amputation, liposuction, rhinoplasty, graft or transplant surgery, a biopsy, skin surgery, breast surgery, prosthetic surgery, fetal surgery, gastroenterologic surgery, thoracic surgery, bladder surgery, heart surgery, liver surgery, pancreas surgery, kidney surgery, lung surgery, gallstone surgery, hernia surgery, shoulder, arm, leg, pelvis, hip, knee, elbow or ankle surgery, uterine or vaginal surgery, blood vessel surgery, prostate surgery, colon or rectal surgery, laser surgery, oral surgery, periodontal surgery, dental implant or tooth repair or extraction.

25. The method of any of claims 1, 2 or 3, wherein the method is performed within 72 hours or less after the surgical or dental procedure.

26. The method of any of claims 1, 2 or 3, wherein the method is performed within 24 hours or less after the surgical or dental procedure.

27. The method of any of claims 1, 2 or 3, wherein the patient is a mammal.

28. The method of any of claims 1, 2 or 3, wherein the patient is a human.

29. The method of any of claims 1, 2 or 3, wherein the patient is a dog, cat, horse, cow, goat, steer or pig.

30. The method of any of claims 1, 2 or 3, wherein the method is performed on a patient within 72 hours of giving birth to a child, or within 24 hours of a cesarean section or episiotomy.

31. The method of any of claims 1, 2 or 3, wherein the method is performed on a patient within 24 hours of giving birth to a child, or within 12 hours of a cesarean section or episiotomy.

32. The method of any of claims 1, 2 or 3, wherein the method is performed on a patient within 12 hours of giving birth to a child, or within 6 hours of a cesarean section or episiotomy.

* * * * *